US00PP31047P2

(12) United States Plant Patent
Heimovaara

(10) Patent No.: US PP31,047 P2
(45) Date of Patent: Nov. 12, 2019

(54) ***CHRYSANTHEMUM* PLANT NAMED 'ZANMUMADORE ORANGE'**

(50) Latin Name: ***Chrysanthemum* x *morifolium* Ramat.**
Varietal Denomination: Zanmumadore Orange

(71) Applicant: Van Zanten Breeding BV, Aalsmeer (NL)

(72) Inventor: Sjoukje Heimovaara, Valkenburg (NL)

(73) Assignee: VAN ZANTEN BREEDING BV (NL)

( * ) Notice: Subject to any disclaimer, the term of this patent is extended or adjusted under 35 U.S.C. 154(b) by 0 days.

(21) Appl. No.: 16/350,057

(22) Filed: Sep. 21, 2018

(51) Int. Cl.
*A01H 5/02* (2018.01)
*A01H 6/14* (2018.01)

(52) U.S. Cl.
USPC ..... Plt./290

(58) Field of Classification Search
USPC ..... Plt./263.1, 286, 287, 290
See application file for complete search history.

*Primary Examiner* — Susan McCormick Ewoldt
*Assistant Examiner* — Karen M Redden
(74) *Attorney, Agent, or Firm* — Steptoe & Johnson LLP

(57) ABSTRACT

A *chrysanthemum* plant named 'Zanmumadore Orange' characterized by its medium sized blooms with bronze ray florets and dark centers and prolific branching; natural season flowering date October 2 (week 41); blooming for a period of 5 weeks.

3 Drawing Sheets

Botanical designation: *Chrysanthemum* x *morifolium* Ramat.

Cultivar denomination: 'Zanmumadore Orange'.

RELATED CULTIVARS

The new plant is a flower color mutant of 'Zanmumadore' (unpatented)

BACKGROUND OF THE INVENTION

The present invention relates to a new and distinct cultivar of *chrysanthemum* plant, botanically known as *Chrysanthemum* x *morifolium* Ramat, commercially known as a garden mum, and hereinafter referred to by the cultivar denomination 'Zanmumadore Orange'. 'Zanmumadore Orange' is a product of a breeding and selection program which had the objective of finding flower color mutants from existing parent plants. The new plant comprises a whole plant mutant of the parent *chrysanthemum* named 'Zanmumadore' (unpatented). Plants from the new cultivar 'Zanmumadore Orange' differ from plants of the parent in the color of the ray-florets. The ray-florets of the parent are pink, while those of the new plant are orange.

In order to obtain color 'Zanmumadore Orange' plants, unrooted cuttings of the parent plant were irradiated in April 2014 at Ziekenhuis, Rotterdam, the Netherlands, with gamma radiation at a dose of 15Gy. These treated cuttings were then planted in a controlled environment (greenhouse) in Rijsenhout, the Netherlands. In this population of planted cuttings, the new cultivar was discovered as a natural flower color mutant in October 2014 by Sjoukje Heimovaara. The first act of asexual reproduction of 'Zanmumadore Orange' was accomplished when after planting of 'Zanmumadore Orange' as a motherplant in December 2014, vegetative cuttings from this 'Zanmumadore Orange' were taken and propagated further in Rijsenhout, the Netherlands. In summer, about 6-8 days are needed to initiate roots in cuttings of the new cultivar, after another 5 days rooted plants are formed. The new cultivar has been found to retain its distinctive characteristics through successive propagations.

BRIEF DESCRIPTION OF THE DRAWINGS

The present invention of a new and distinct variety of *chrysanthemum* (of about 22 weeks) is shown in the accompanying drawings, the color being as nearly true as possible with color photographs of this type.

DESCRIPTION OF THE INVENTION

Figure 1:
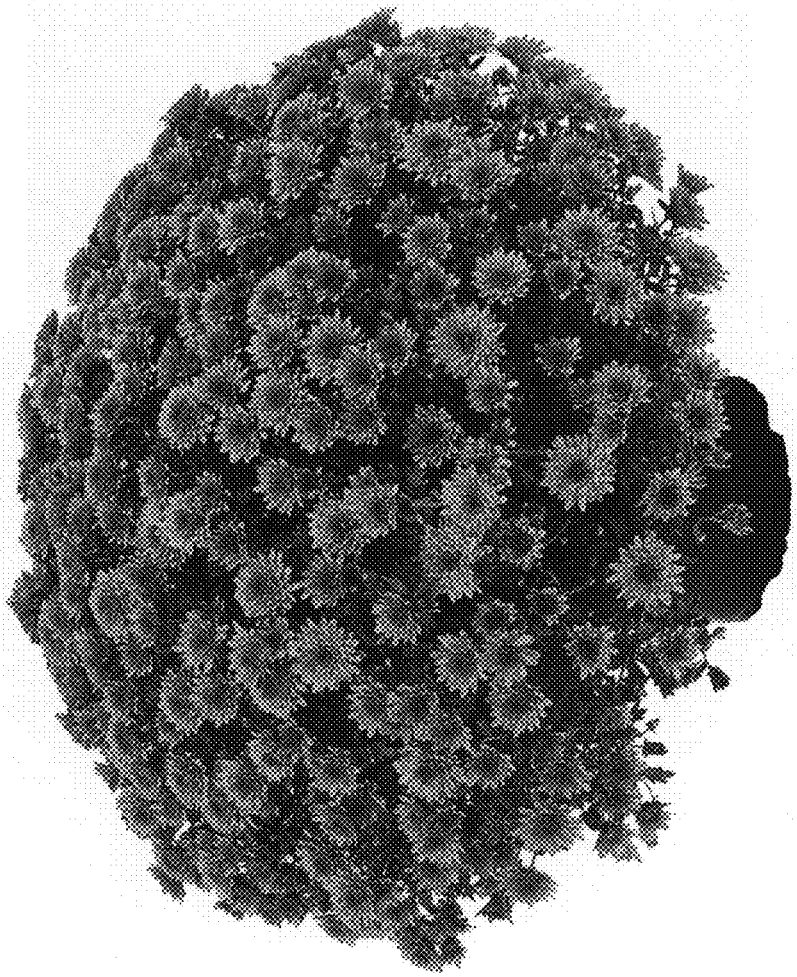
FIG. 1 shows a plant of the cultivar in full bloom.
Figure 2:
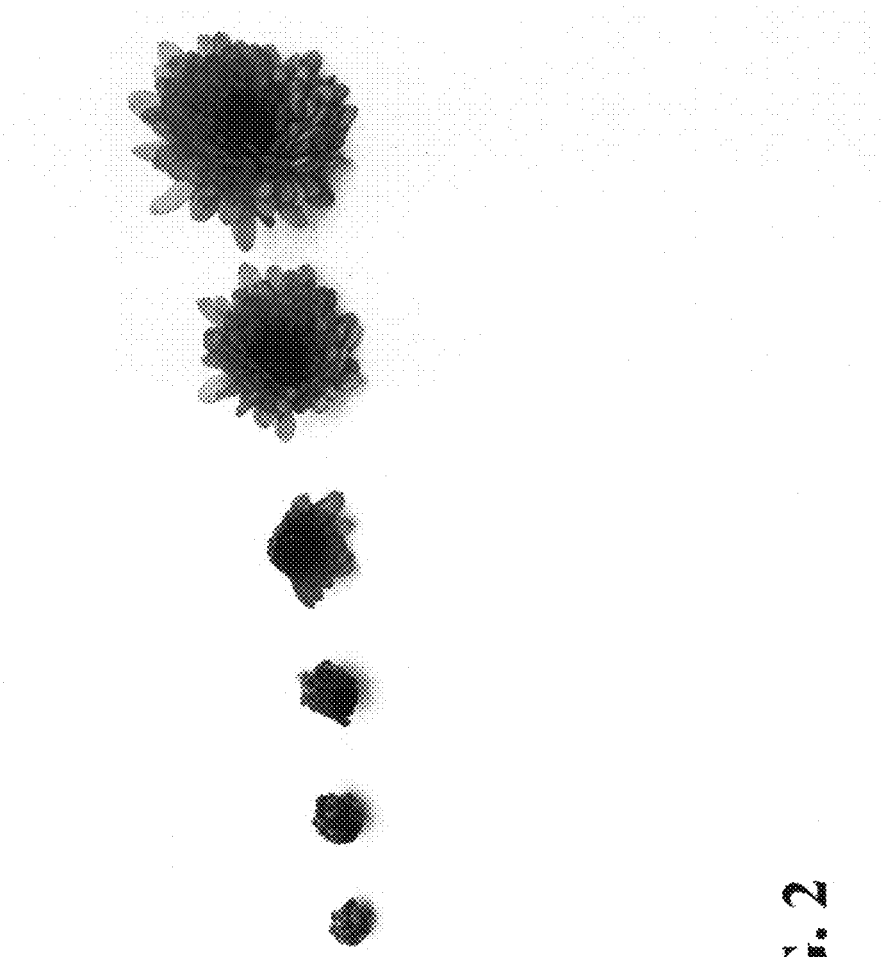
FIG. 2 shows the various stages of blooms of the new cultivar.
Figure 3:
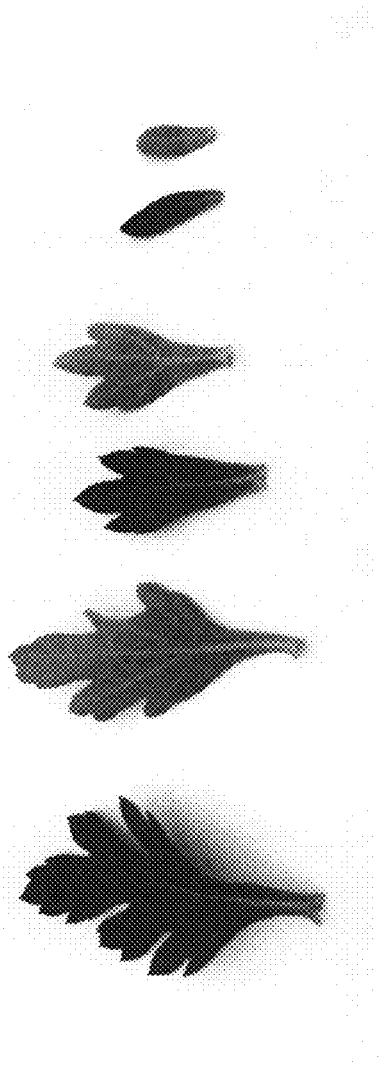
FIG. 3 shows the various stages of foliage of the new cultivar.

The observations and measurements were gathered from plants in the period of 19 to 25 weeks of age grown outdoors in Rijsenhout, the Netherlands, under natural day length and temperature and planted in week 22 in 2017. The natural blooming date of this crop was October 2 (week 41). The average height of the plants was 25-30 cm. No growth retardants were used. No tests were done on disease or insects resistance or susceptibility. No tests were done on cold or drought resistance. This new variety produces medium sized blooms with bronze ray florets and a dark center blooming for a period of five weeks.

From the cultivars known to the inventor, the most similar existing cultivars in comparison to 'Zanmumadore Orange' are its parents 'Zanmumadore' and 'Zanmumadore Red' (unpatented). When 'Zanmumadore', 'Zanmumadore Orange' and 'Zanmumadore Red' are being compared the following differences are noticed: ray floret color in 'Zanmumadore' is pink, bronze in 'Zanmumadore Orange' and red in 'Zanmumadore Red'.

The following is a description of the plant and characteristics that distinguish 'Zanmumadore Orange' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour chart, sixth edition, 2015.

Botanical Description of *Chrysanthemum* x *morifolium* Ramat. 'Zanmumadore Orange'

Bud:
- *Size*.—Small; cross-section 5 mm, height 4 mm.
- *Shape*.—Round.
- *Texture*.—Pubescent.
- *Outside color*.—Greyed-green 191A.

Phyllaries:
- *Number*.—24, arranged in 3 rows.
- *Shape*.—Elliptic.
- *Apex*.—Acute.
- *Base*.—Truncate.
- *Margin*.—Entire.
- *Color*.—Upper side: Green 139A. Lower side: Green N138C.
- *Length and width*.—0.6-0.8 mm; 2-4 mm.
- *Texture*.—Pubescent.

Inflorescences:
- *Type*.—Double.
- *Height*.—13 cm.
- *Diameter*.—3.5-4 cm.
- *Peduncle length*.—6-7 cm.
- *Peduncle color*.—Green 138B.
- *Peduncle diameter*.—1.5 mm.
- *Peduncle texture*.—Pubescent.
- *Peduncle strength*.—Medium.
- *Number per branch*.—About 8-9 inflorescences.
- *Duration of flowering*.—5 weeks.
- *Seeds*.—Produced in small quantities, ovate, Greyed-brown 199A, length 1.5 mm, diameter 0.5 mm; texture: rough with ribs.
- *Fragrance*.—Faint *chrysanthemum* odor.

Color inflorescences:
- *Center of inflorescence*.—Immature stage: Greyed-red 178A; Mature stage: Greyed-red 178A.
- *Color of upper side of ray florets* (*outer rows*).—Greyed-orange 163C.
- *Color of lower side of ray florets* (*outer rows*).—Greyed -orange 166B.
- *Color of upper side ray florets* (*inner rows*).—Greyed-red 178A.
- *Color of lower side ray-florets* (*inner rows*).—Greyed-red 178C.
- *Tonality from distance*.—A garden mum with bronze blooms and a dark center.
- *Color of ray florets after aging of the plant*.—Greyed-orange 168C.

Ray florets:
- *Number of types*.—2.
- *Type*.—Ligulate.
- *Rows*.—About 15.
- *Texture*.—Upper and lower side smooth.
- *Number*.—Outer rows: 140; inner rows: 30.
- *Shape*.—Outer rows: elliptic; inner rows: narrowly elliptic.
- *Apex*.—Outer rows: dentate; inner rows: dentate.
- *Base*.—Attenuate.
- *Cross-section*.—Outer rows: flat; inner rows: concave.
- *Longitudinal axis*.—Outer rows: straight; inner rows: straight.
- *Length of corolla tube*.—3 mm.
- *Diameter corolla tube*.—1 mm.
- *Ray floret margin*.—Entire.
- *Ray floret length* (*outer rows*).—1.5-2 cm.
- *Ray-floret length* (*inner rows*).—0.8-1 cm.
- *Ray-floret width* (*outer rows*).—3 mm.
- *Ray floret width* (*inner rows*).—1 mm.
- *Ratio length/width*.—Medium.

Disc florets: Absent.

Receptacle:
- *Color*.—Yellow-green 145D.
- *Shape*.—Domed raised.
- *Height*.—3-4 mm.
- *Diameter*.—4 mm.

Reproductive organs:
- *Androecium*.—Absent.
- *Pollen*.—Lacking.
- *Gynoecium*.—Present on ray florets.
- *Style color*.—Yellow-green 154C.
- *Style length*.—4 mm.
- *Stigma color*.—Yellow 7A.
- *Stigma width*.—1 mm.
- *Ovary*.—Enclosed in calyx.
- *Ovary color*.—Yellow-green 149D.

Plant:
- *Type*.—Bushy.
- *Growth habit*.—Spherical shape.
- *Growth rate*.—High.
- *Height*.—25-30 cm.
- *Width*.—40-45 cm.
- *Stem color*.—Greyed-brown 199A.
- *Stem strength*.—Not strong.
- *Stem brittleness*.—Brittle.
- *Stem anthocyanin coloration*.—Absent.
- *Internode length*.—0.5-2.5 cm.
- *Length of lateral branch*.—From top to bottom 20-22 cm.
- *Lateral branch color*.—Green 137 C.
- *Lateral branch, attachment*.—Weak.
- *Lateral branch diameter*.—3 mm.
- *Lateral branch texture*.—Pubescent with ribs.
- *Branching* (*average number of lateral branches*).—Medium with 8 breaks after pinching.
- *Natural season blooming date*.—October 2 (week 41) in Rijsenhout, the Netherlands.
- *Root habits*.—Fine, freely branching.
- *Root color*.—White 155D.
- *Rooting time*.—6-8 days.
- *Formation rooted plants*.—12-14 days.

Foliage:
- *Leaf glossiness*.—Upper side: very weak. Lower side: absent.
- *Leaf color*.—Upper side: Green 136A. Lower side: Green 137A.
- *Color midvein*.—Upper side: Yellow-green 147D. Lower side: Yellow-green 148D.
- *Size*.—Small; length 3-5 cm, width 0.5-2.5 cm.
- *Quantity* (*number per lateral branches*).—About 25.

*Shape*.—Elliptic to obovate.
*Texture upper side*.—Sparsely pubescent.
*Texture under side*.—Pubescent.
*Venation arrangement*.—Pinnate.
*Shape of margin*.—Serrated.
*Shape of base of sinus between lateral lobes*.—Rounded.
*Margin of sinus between lateral lobes*.—Diverging.
*Shape of base*.—Acute.
*Apex*.—Mucronulate.
*Petiole attitude*.—Moderately upwards.
*Petiole length*.—0.1-0.8 cm.
*Petiole diameter*.—3 mm.
*Petiole color*.—Yellow-green 147D.
*Stipules*.—Present, small.

TABLE 1

Differences with the comparison variety, when grown under identical conditions

| | 'Zanmumadore' | 'Zanmumadore Orange' | 'Zanmumadore Red' |
|---|---|---|---|
| Color upper side ray floret-outer row | Red-purple 72C | Greyed-orange 163C | Greyed-red 178A |
| Color upper side ray floret color-inner row | Red-purple 72A | Greyed-red 178A | Greyed-purple 187B |

I claim:

1. A new and distinct *chrysanthemum* plant named 'Zanmumadore Orange' as described and illustrated.

* * * * *